United States Patent [19]

Erbs

[11] Patent Number: 5,168,754
[45] Date of Patent: Dec. 8, 1992

[54] METHOD AND APPARATUS FOR DETECTING ROOM HUMIDITY

[75] Inventor: Daryl G. Erbs, Palermo, N.Y.

[73] Assignee: Carrier Corporation, Syracuse, N.Y.

[21] Appl. No.: 816,001

[22] Filed: Jan. 2, 1992

[51] Int. Cl.$^5$ .......................... G01K 3/08; G01W 1/00
[52] U.S. Cl. ................................ 73/335.02; 374/10; 374/109
[58] Field of Search ................. 374/10, 109; 364/557; 73/29.02, 335

[56] References Cited

U.S. PATENT DOCUMENTS

| | | | |
|---|---|---|---|
| 1,481,251 | 1/1924 | Braemer et al. | 73/335.09 |
| 1,636,350 | 7/1927 | Armstrong | 73/335.09 |
| 2,157,685 | 5/1939 | Anderson | 73/335.11 |
| 3,080,465 | 3/1963 | Pelishek | 374/109 |
| 3,110,173 | 11/1963 | Bishop | 73/29.02 |
| 3,599,862 | 8/1971 | Hogan et al. | 73/335.03 |
| 4,703,886 | 11/1987 | Kirby | 73/335.04 |
| 4,853,693 | 8/1989 | Eaton-Williams | 364/557 |

FOREIGN PATENT DOCUMENTS 0107953  4/1990  Japan ................................ 73/29.02

*Primary Examiner*—Hezron E. Williams
*Assistant Examiner*—George M. Dombroske

[57] ABSTRACT

A method for determining the relative humidity in an interior space without using a special humidity sensor, the method including passing a flow of air of known temperature and humidity through the cooling coil of a known air conditioning system for a pre-determined period of time. The temperature of the air exiting from the cooling coil after the pre-determined period of time is measured. A reference temperature differential is determined by subtracting the exiting temperature from the known temperature of the entering air. A flow of air for which it is desired to know the relative humidity is then passed through the cooling coil for the same pre-determined period of time. The temperature of the air entering the cooling coil and exiting from the cooling coil at the end of this pre-determined period of time is determined. The exit temperature is subtracted from the entering temperature to provide the temperature differential for the air of unknown relative humidity. The reference temperature differential is then compared to the calculated temperature differential. If the temperature differential is smaller than the reference temperature differential the air is then known to be more humid than the known relative humidity. If the temperature differential is the same, the relative humidity is the same, and, if the temperature differential is greater the air is less humid than the known relative humidity.

1 Claim, 2 Drawing Sheets

METHOD AND APPARATUS FOR DETECTING ROOM HUMIDITY

BACKGROUND OF THE INVENTION

1. Field of the Invention

The present invention relates to a method and apparatus for determining relative humidity in the air passing through the evaporator of an air conditioner.

2. Description of the Prior Art

A well designed complete air conditioning system is capable of achieving the following goals:
1. Temperature control;
2. Humidity control;
3. Air movement and circulation; and
4. Air filtering, cleaning and purification.

In most residential air conditioning installations good engineering of the system including the compressor, heat exchangers, fans expansion devices and other controls result in accurate temperature control to a desired set point. Humidity control generally is achieved by movement of the inside air past the evaporator coil to reduce the temperature of the moisture laden air to at least the dew point temperature in order for moisture to condense out the air. Humidity controls for the operator to set, or, for that matter, automatic control of dehumidification is norma not provided in such systems as accurate humidity sensors are quite expensive.

With the development of air conditioning systems making use of variable speed motors for driving the compressor and fans it has become possible for an air conditioning system to be operated in different modes of operation depending upon the relative humidity level in the air being cooled. In order to make use of such capability it is necessary for the microprocessor controller of such a system to have an input from a humidity measuring device. As pointed out above, such devices are quite expensive and do not lend themselves to being economically incorporated into a small room or residential air conditioning system.

SUMMARY OF THE INVENTION

It is an object of the present invention to detect the relative humidity in an interior space without using a special sensor designed to detect relative humidity.

This and other objects of the present invention are carried out by passing a flow of air of known temperature and humidity through the cooling coil of a known air conditioning system for a pre-determined period of time. The temperature of the air exiting from the cooling coil after the pre-determined period of time is measured. A reference temperature differential is determined by subtracting the exiting temperature from the known temperature of the entering air. A flow of air for which it is desired to know the relative humidity is then passed through the cooling coil for the same pre-determined period of time. The temperature of the air entering the cooling coil and exiting from the cooling coil at the end of this pre-determined period of time is determined. The exit temperature is subtracted from the entering temperature to provide the temperature differential for the air of unknown relative humidity. The reference temperature differential is then compared to the calculated temperature differential. If the temperature differential is smaller than the reference temperature differential the air is then known to be more humid than the known relative humidity. If the temperature differential is the same, the relative humidity is the same, and, if the temperature differential is greater the air is less humid than the known relative humidity.

BREIF DESCRIPTION OF THE DRAWINGS

The novel features that are considered characteristics of the invention are set forth with particularity in the appended claims. The invention itself, however, both as to its organization and its method of operation, together with additional objects and advantages thereof, will best be understood from the following description of the preferred embodiment when read in connection with the accompanying drawings wherein like numbers have been employed in the different figures to denote the same parts, and wherein;

DETAILED DESCRIPTION OF THE PREFERRED EMBODIMENT

Figure 1:
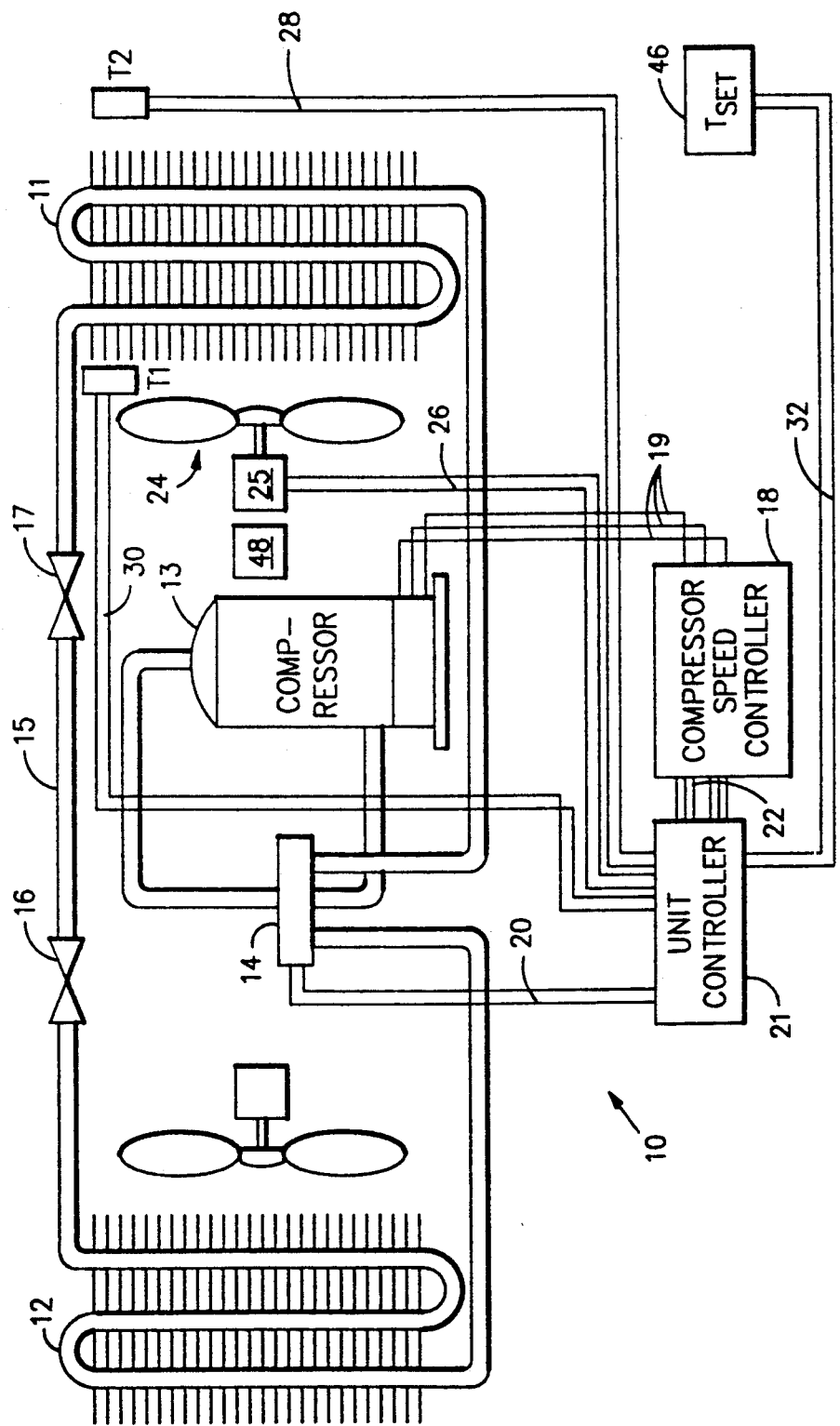
FIG. 1 is a schematic illustration of a heat pump system having the present invention incorporated therein.

Referring now to FIG. 1, there is shown a heat pump system 10 which includes an indoor coil 11, an outdoor coil 12, a compressor 13 and a reversing valve 14. Installed in the line 15 between the indoor and outdoor coils 11 and 12 are expansion valves 16 and 17 each of which has a provision for bypassing refrigerant when it is not acting as an expansion device. All of these components operate in a conventional manner to provide a cooling function while operating in the air conditioning mode and a heating function while operating in a heat pump mode.

As illustrated the heat pump system 10 is equipped with a variable speed compressor driven by a variable speed motor such as, for example, an electronically commutated motor (ECM) or an inverter driven AC induction motor. The compressor 13 is normally located outdoors in an enclosure with the outdoor coil 12. A compressor speed controller 18 is provided to communicate with and to coordinate the operation of the compressor and its associated equipment.

The compressor speed controller 18 is electrically connected to the compressor 13 by electrical leads 19, and, to a unit controller 21 by leads 22. The unit controller 21 is also connected to the reversing valve 14 by electrical leads 20 and to a multiple speed electric motor associated with an indoor coil fan 24 via electrical leads 26. The unit controller 21 is also connected to an indoor coil discharge air temperature sensor T2 via leads 28 and to a room air or indoor coil entering air temperature sensor T1 via electrical leads 30. Finally, for purposes of the description of the invention the unit controller is connected to a room thermostat 46 via appropriate electrical leads 32. The temperature set by the user at the thermostat will hereinafter be referred to as T set. The unit controller 21 is also usually adapted to control other system components, however, for purposes of this illustration and description of the present invention such interconnections are not shown in the drawing in order to simplify description of the invention.

The unit controller 21 comprises a programmable microprocessor which has been programmed to operate the heat pump system in several different modes of operation. Included among those modes is a mode hereinafter identified as "auto" wherein the system is set to automatically bring the room temperature to the temperature set by the room thermostat T set. In this mode the system will operate in a mode of operation which is decided by the microprocessor, based on the room conditions and the temperature set point, T set, which is adjustable by the user. In the auto mode the system may select, as necessary, a heating mode, or an off mode or one of two cooling modes of operation. One cooling mode is a "normal" cooling mode of operation which the system runs in if the room humidity is determined to be "normal". The other cooling mode is referred to as the "dry" mode in which the system operates if the room is determined to be "humid".

According to the present invention the microprocessor of the unit controller 21 has been programmed with data relating to the capabilities of the specific components of the heat pump system which it is controlling. This data enables the controller to process the inputs from the inlet air temperature thermistor T1 and the discharge air temperature thermistor T2 when the system is operating at given conditions and to make a decision as to whether the air in the room is humid and accordingly whether the system should operate in the dry or the cooling mode of operation.

Looking now at FIG. 2 the principals of the present invention will be described in connection with a simplified psychrometric chart. The psychrometric chart is a graph of the temperature-pressure relationship of steam (water vapor). The horizontal scale represents dry bulb temperatures in degrees F°. The values along the vertical scale represents grains of moisture per pound of dry air. The 100% humidity line or the line of saturation is identified by reference numeral 34. Other lines of lower relative humidity are substantially parallel to and to the right of the saturation line 34 and only one of those lines identified by the legend RH and bearing the reference numeral 36 is shown in the drawing. This line, for purposes of illustration, represents the 70% relative humidity line. Values of relative humidity higher than the 70% level would lie to the left of the 70% line 36 while values of relative humidity less than the 70% line 36 would lie to the right of the 70% line 36.

According to the present invention the data necessary in order to program the microprocessor for use with a particular air conditioning system is obtained by running the system at a given set of operating conditions with an air flow across the evaporator or indoor coil 11 at known temperature and humidity conditions. Apparatus for providing such a flow of air is represented generally be reference number 48.

For example, in a system of the type illustrated in FIG. 1 with a variable speed compressor, a specific compressor speed and a specific indoor fan speed is set and run for a predetermined period of time. As a specific example, in one system the indoor fan is set to low speed and the compressor set to run at 45 hertz. A supply of air having a dry bulb temperature of 70° F. and a relative humidity of 70% is allowed to flow past the indoor coil 11 for a period of six minutes. At the end of the six minute period, the difference between the room air temperature as measured by thermistor T1 and the discharge air temperature as measured by thermistor T2 was calculated. This difference was designated as $\Delta T$ ref.

Figure 2:
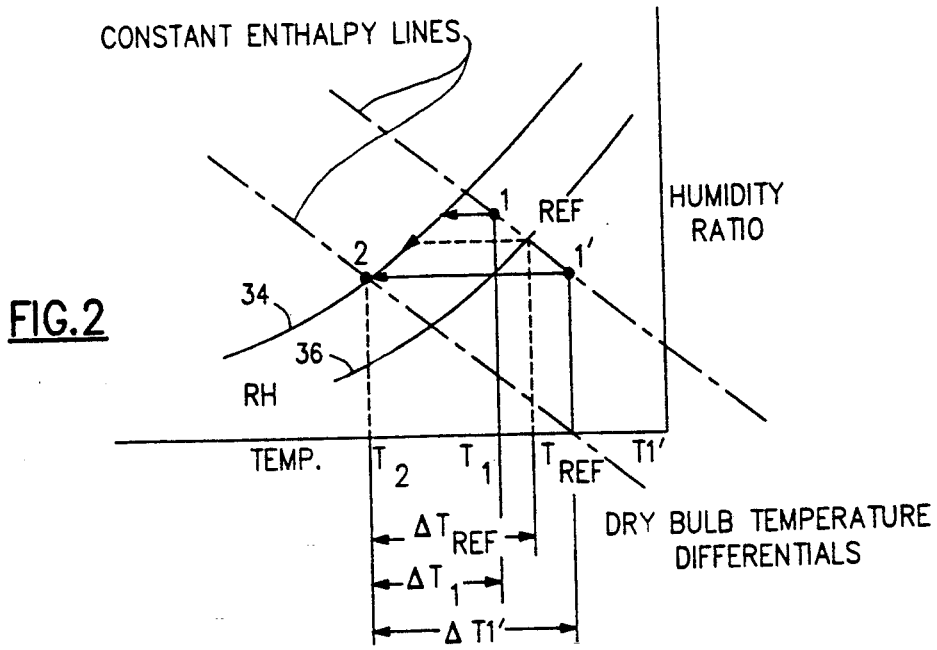
FIG. 2 is a simplified psychrometric chart showing the principles of the present invention.

Referring to FIG. 2 this information is recorded on the phsycrometric chart. The 70° F. dry bulb temperature is identified on the horizontal scale by the point identified as T ref. Following the dotted line vertically from the point T ref the intersection with the 70% relative humidity line 36 identifies the point identified as "ref". T ref accordingly represents the 70° room air temperature measured by the thermistor T1 in the above described test. The temperature T2 on the horizontal temperature scale represents the temperature in the test described, of the air exiting from the indoor coil 11 as measured by the thermistor T2. Again, following the dotted line vertically upwardly to the saturation curve defines point 2, i.e. the conditions of the air exiting from the indoor coil during the test. Accordingly, following the path from the point identified as "ref" to point 2 it will be noted that the temperature of the air decreased from the point "ref" to the left to the intersection with the saturation curve without removing any moisture therefrom, and, from the intersection with the saturation curve moved downwardly and to the left further reducing the temperature and reducing, the amount of moisture in the air. The term identified as $\Delta$ T ref is indicated below the dry bulb temperature axis as being the difference between the temperature at the point "ref" and the point 2.

For the given system for which the value of the term $\Delta$ T ref has been determined this value is programmed into the micro processor and is looked at by the system during operation to, compare an actual $\Delta$ T to this value. If the actual $\Delta 0$ T is less than the $\Delta$ t ref as illustrated by the example identified as $\Delta$ T 1 in FIG. 2 it will be known that the relative humidity of the room air, as identified by the data of point 1, is greater than the 70% relative humidity. Likewise, if the $\Delta$ T is greater that the $\Delta$ T ref as identified by the example $\Delta$ T 1', and the corresponding data point "1'" it will be known by comparison to $\Delta$ T ref that the relative humidity is less than the 70% reference relative humidity. As will be seen now in connection with the description of the programmed logic of FIG. 3, given this information, the microprocessor will run the system in the normal cooling or dry mode as necessary.

Figure 3:
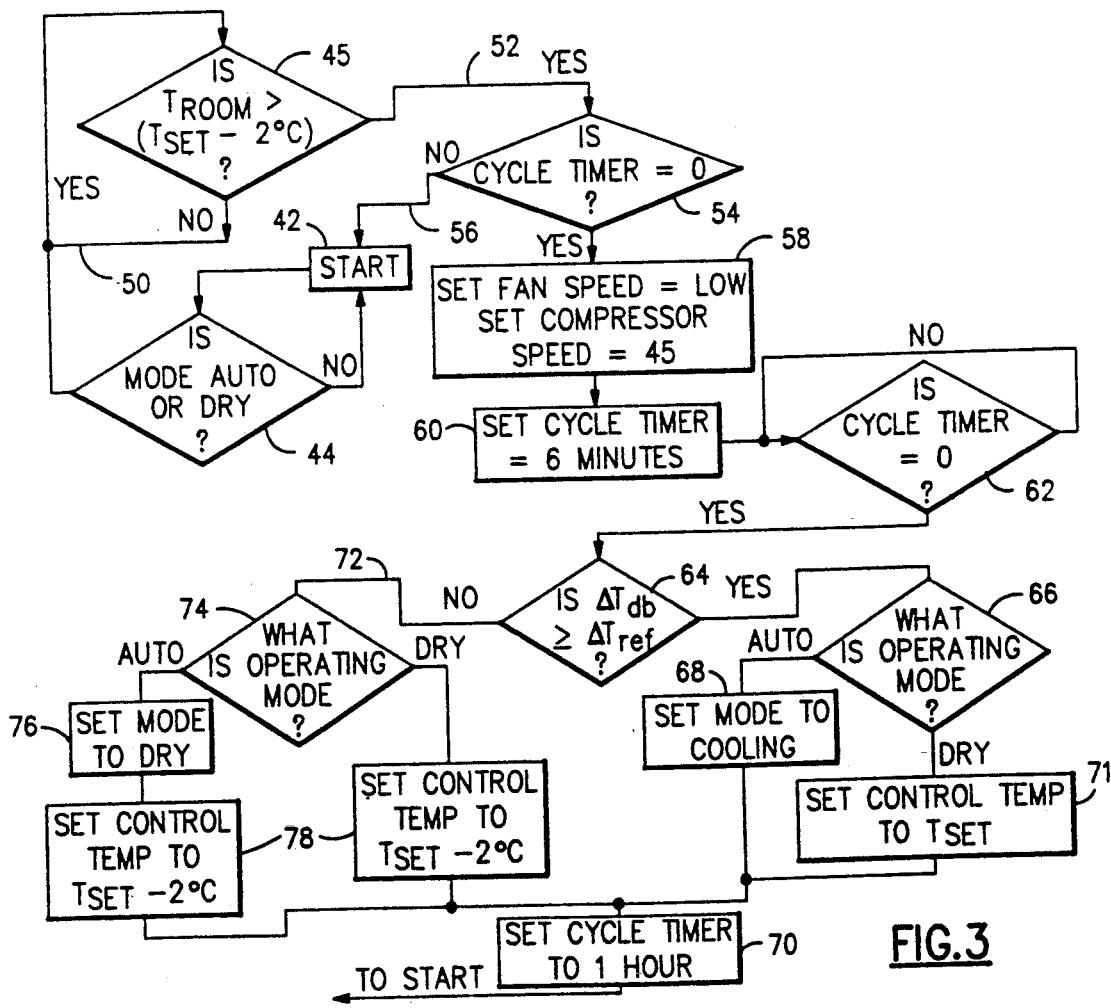
FIG. 3 is a flow chart showing the logic programmed into the microprocessor of the heat pump system of FIG. 1.

Looking now at FIG. 3 the logic programmed into the microprocessor to carry out the determination of whether the system should operate in the normal cool or dry mode is illustrated. Beginning at the block 42 labeled "start" the first step performed (44) is to ascertain the current mode of operation of the system. If the system is in the automatic or dry mode of operation the system moves to step 45. If the system is not in auto or dry i.e., in heat or off, no action will be taken. In step 45 the controller ascertains whether the room temperature (as measured by thermistor T1) is warmer than 2° centigrade below the setpoint T set. If it is not the system continues to make this comparison via path 50 until such condition is reached. If the room temperature is warmer than 2° centigrade below the setpoint the system moves via path 52 to step 54 to inquire as to the status of the cycle timer which is contained within the micro processor. If the cycle timer is not at 0 it means that the cycle timer is performing its timing function for a particular event, as will be seen and the system passes via path 56 back to start 42. If the cycle timer is equal to 0 the system then proceeds to step 58 to set the system to the predetermined conditions which will allow the $\Delta$ T at current conditions to be calculated to allow determination of the relative humidity. Accordingly as indicated in step 58 the fan speed is set to low speed and the compressor speed is set to 45 hertz. Once these conditions have been set, the cycled timer is set for the predetermined period of six minutes as indicated by step 60. The system then continues in a holding pattern as indicated by step 62 until the cycled timer counts down to 0.

When the six minute period is over and the system is at substantially steady state conditions, the system proceeds to step 64 where the temperature differential ascertained by the thermistors T1 and T2 has been calculated as Δ T db, and, this value is compared to the Δ T ref which is stored in the micro processor. If the Δ T db is greater than or equal to the Δ T reference it indicates that the relative humidity in the room is less than the 70% reference humidity and the system moves on to step 66 where the mode of operation of the system is ascertained. If the system is in the automatic mode it is then set to normal cooling at step 68 and the cycle timer is set for one hour as indicated in step 70. At this point, once an hour, at the start of the next compressor "on" cycle after the hour has elapsed, the unit will re-evaluate the room humidity state as described above beginning at the normal start point 42. If it is determined at step 66 that the system is operating in the dry mode of operation the system control temperature will be returned to the selected thermostat setting T set. This step 11 will be better understood after reading the description of the shifting of the system to the dry mode of operation.

Returning now to step 64, if it is ascertained that the Δ T db is not greater than or equal to the Δ T REF the system then knows that the relative humidity in the room is greater than the reference humidity of 70% and the microprocessor follows the no path 72 to step 74. At step 74 the inquiry is made as to whether the system is in the auto or the dry mode of operation. If the system is in the auto mode it is immediately reset to the dry mode as indicated by step 76. At this point regardless of the path followed the system is in the dry mode and as indicated in the two boxes, identified by reference number 78 a temporary set point T set is created by the microprocessor by subtracting 2° C. from the actual set point set of the room thermostat 46. This allows the system to continue operating in the dry mode even after the set point temperature has been reached in order to remove the excess humidity from the room air. Accordingly, this temporary control set point will operate in place of the thermostat set point. During a typical dry mode of operation the indoor fans speed would be reduced in order to increase the residence time of the room air in contact with the inside coil 11 and thereby to facilitate condensation of moisture from the air.

Following the setting of the temporary setpoint it will be noted that the cycle timer is again set to one hour so that the system will operate in the dry mode with the temporary set point. Following this, once an hour, at the start of the next compressor "on" cycle, after the hour has elapsed, the unit will re-evaluate the humidity state beginning at the start step 42 following the procedure described above.

What is claimed:

1. A method of detecting relative humidity of air being passed in heat exchange relationship with a cooling coil comprising the steps of:
   a. passing a flow of air of known temperature and relative humidity through the cooling coil for a pre-determined period of time;
   b. determining the temperature of the air exiting from the cooling coil after the pre-determined period of time;
   c. calculating a reference temperature differential by subtracting the exiting temperature from the known temperature;
   d. passing a flow of air for which it is desired to know the relative humidity through the cooling coil for the same pre-determined period of time;
   e. determining the temperature of the air entering the cooling coil after the pre-determined period of time;
   f. determining the temperature of the air exiting from the cooling coil after the pre-determined period of time;
   g. calculating the temperature differential by subtracting the exit temperature from the entrance temperature;
   h. comparing the reference temperature differential to the temperature differential calculated in step g, if the temperature differential is smaller than the reference temperature differential the air is more humid than the known relative humidity, if the temperature differential is the same the relative humidity is the same, and if the termperature differential is greater the air is less humid than the known relative humidity.

* * * * *